(12) United States Patent
Smith

(10) Patent No.: US 7,338,440 B1
(45) Date of Patent: Mar. 4, 2008

(54) LARYNGOSCOPE SYSTEM WITH ILLUMINATOR AND SUCTION CAPABILITIES

(76) Inventor: John D. Smith, 2321 Needham Dr., Valrico, FL (US) 33594

( * ) Notice: Subject to any disclaimer, the term of this patent is extended or adjusted under 35 U.S.C. 154(b) by 466 days.

(21) Appl. No.: 11/002,050

(22) Filed: Dec. 2, 2004

(51) Int. Cl.
*A60B 1/267* (2006.01)

(52) U.S. Cl. .................. 600/187; 600/185; 600/190; 600/193; 600/197

(58) Field of Classification Search ............... 600/185, 600/187, 188, 190, 193, 199, 194, 205, 210, 600/213
See application file for complete search history.

(56) References Cited

U.S. PATENT DOCUMENTS

| | | | | |
|---|---|---|---|---|
| 3,638,644 A | * | 2/1972 | Reick | 600/191 |
| 4,126,127 A | * | 11/1978 | May | 600/187 |
| 4,799,485 A | * | 1/1989 | Furey et al. | 600/193 |
| 4,947,896 A | * | 8/1990 | Bartlett | 600/187 |
| 5,702,351 A | * | 12/1997 | Bar-Or et al. | 600/190 |
| 5,897,489 A | * | 4/1999 | Urbanowicz et al. | 600/185 |
| 6,248,061 B1 | * | 6/2001 | Cook, Jr. | 600/187 |
| 6,251,069 B1 | * | 6/2001 | Mentzelopoulos et al. | 600/196 |
| 6,569,089 B1 | * | 5/2003 | Covington et al. | 600/199 |
| 6,991,604 B2 | * | 1/2006 | Cantrell | 600/194 |

* cited by examiner

*Primary Examiner*—John P. Leubecker
*Assistant Examiner*—Victoria W Chen
(74) *Attorney, Agent, or Firm*—Edward P. Dutkiewicz

(57) ABSTRACT

A laryngoscope system has a blade with a distal end, and intermediate extent, and a generally C-shaped recess adjacent to a proximal end. A handle has a lower end, a central extent, and an upper end. The lower end has a space between two parallel shoulders to receive the blade and a pin spanning the space to rotatably support the recess of the blade. A suction subassembly extends between the blade and the handle. An optical subassembly extends between the blade and the handle. The blade and optical subassembly move between an operative position and inoperative position.

4 Claims, 4 Drawing Sheets

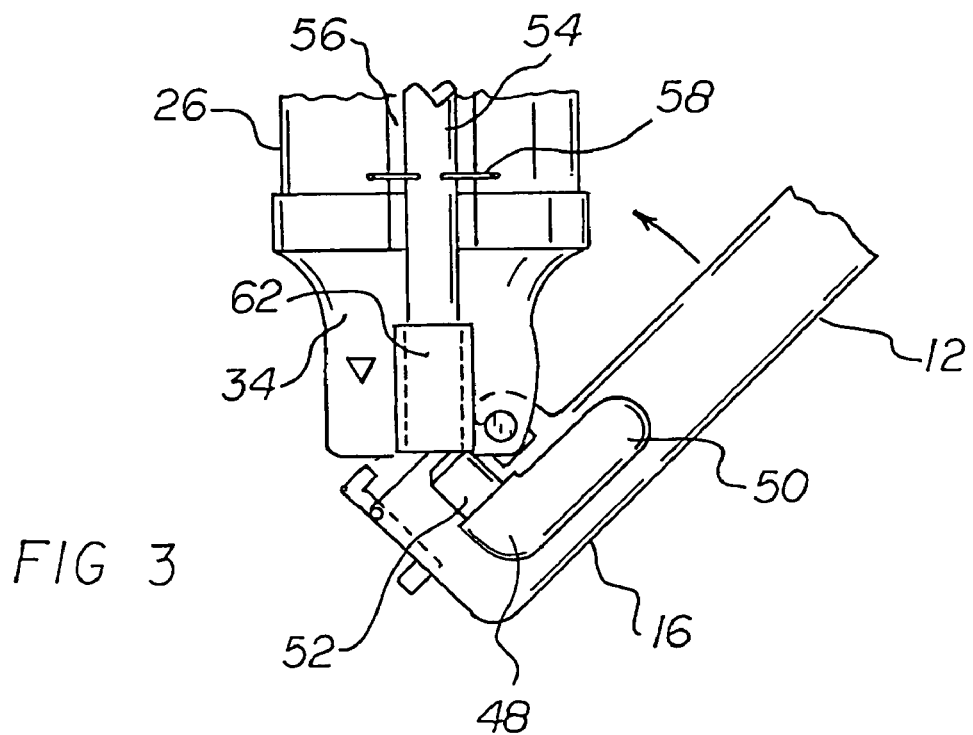
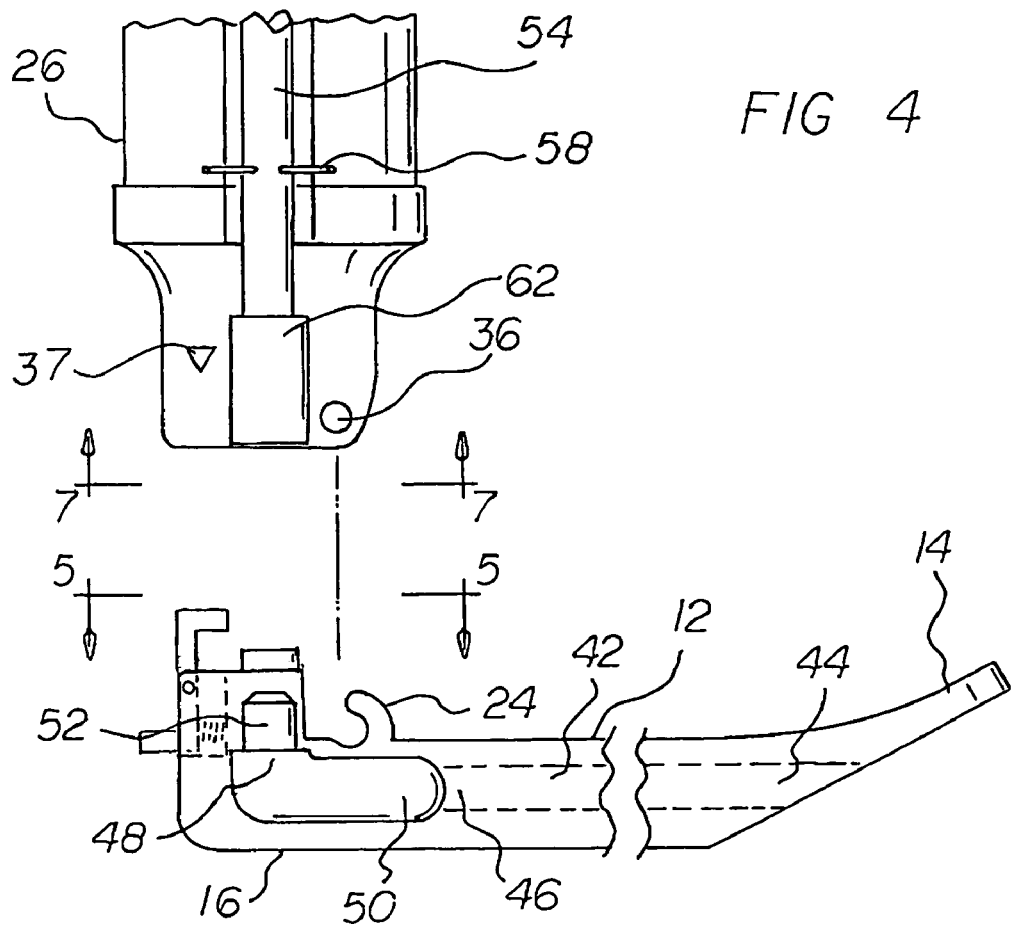

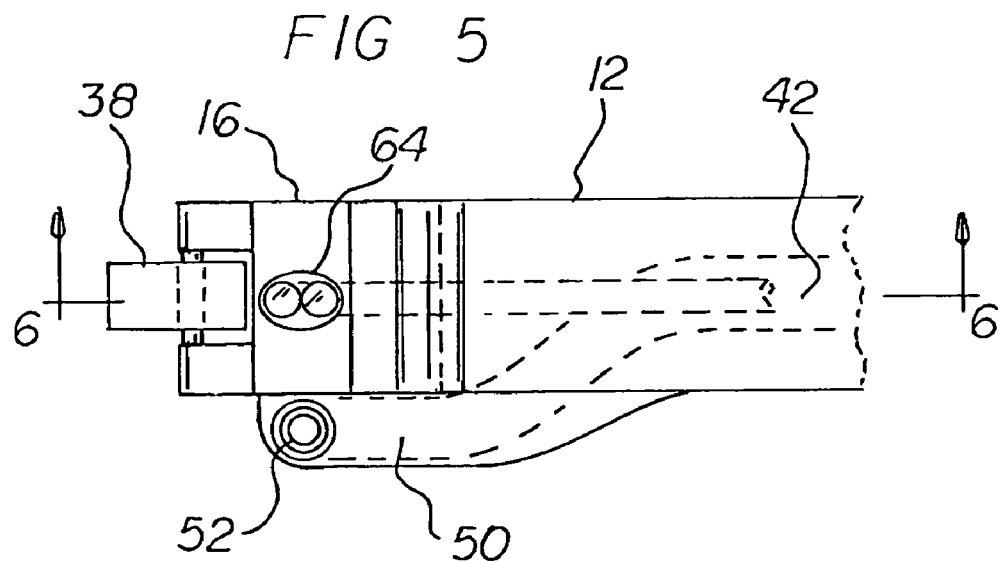
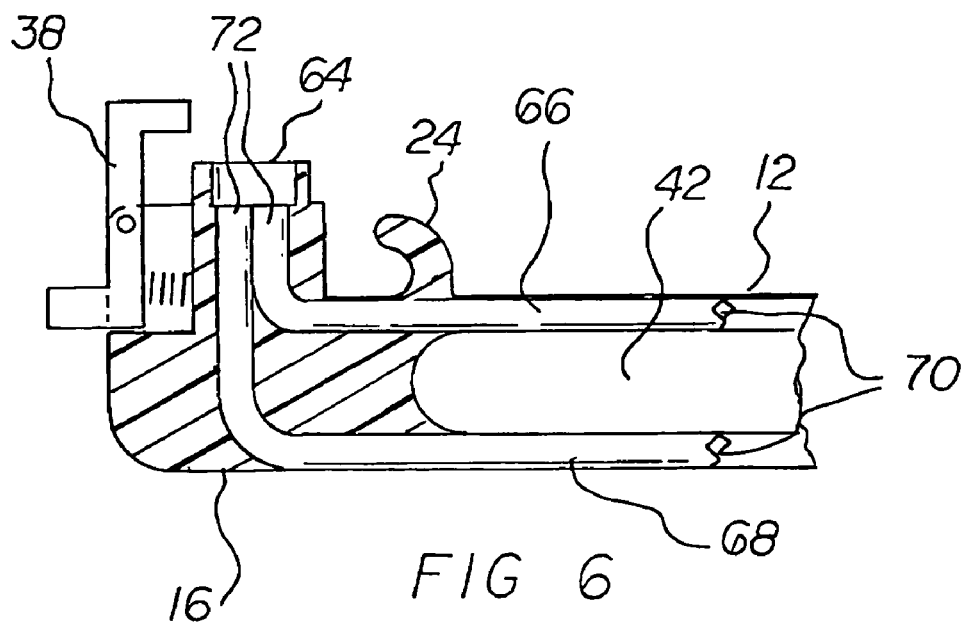

LARYNGOSCOPE SYSTEM WITH ILLUMINATOR AND SUCTION CAPABILITIES

BACKGROUND OF THE INVENTION

1. Field of the Invention

The present invention relates to a laryngoscope system with illuminator and suction capabilities and more particularly pertains to facilitating endotracheal intubation.

2. Description of the Prior Art

The use of laryngoscopes of known designs and configurations is known in the prior art. More specifically, laryngoscopes of known designs and configurations previously devised and utilized for intubations are known to consist basically of familiar, expected, and obvious structural configurations, notwithstanding the myriad of designs encompassed by the crowded prior art which has been developed for the fulfillment of countless objectives and requirements.

By way of example, U.S. Pat. No. 6,569,089 to Covington et al. describes a lighted intubating laryngoscope. U.S. Pat. No. 5,363,838 to George discloses a fiberoptic intubating scope with camera and lightweight portable screen and method of using the same. U.S. Pat. No. 4,742,819 to George discloses an intubating scope with camera and screen. U.S. Pat. No. 4,306,547 to Lowell discloses a rigid fiberoptic laryngoscope. Lastly, U.S. Pat. No. 4,126,127 to May discloses a suctioning/oxygenating laryngoscope blade.

While these devices fulfill their respective, particular objectives and requirements, the aforementioned patents do not describe laryngoscope system with illuminator and suction capabilities that facilitates endotracheal intubation.

In this respect, the laryngoscope system with illuminator and suction capabilities according to the present invention substantially departs from the conventional concepts and designs of the prior art, and in doing so provides an apparatus primarily developed for the purpose of facilitating endotracheal intubation.

Therefore, it can be appreciated that there exists a continuing need for a new and improved laryngoscope system with illuminator and suction capabilities which can be used for facilitating endotracheal intubation. In this regard, the present invention substantially fulfills this need.

SUMMARY OF THE INVENTION

In view of the foregoing disadvantages inherent in the known types of laryngoscopes of known designs and configurations now present in the prior art, the present invention provides an improved laryngoscope system with illuminator and suction capabilities. As such, the general purpose of the present invention, which will be described subsequently in greater detail, is to provide a new and improved laryngoscope system with illuminator and suction capabilities and method which has all the advantages of the prior art and none of the disadvantages.

To attain this, the present invention essentially comprises a blade. The blade is fabricated of an essentially rigid, preferably plastic, material. The blade has a distal end positionable in a patient's mouth, a proximal end positionable outside of a patient's mouth. The blade also has an intermediate extent between the proximal and distal ends. The blade has an upper surface positionable on a patient's tongue and a lower surface. The blade having a generally C-shaped recess adjacent to the proximal end of the upper surface.

Next provided is a handle fabricated of an essentially rigid, preferably stainless steel, material. The handle has a lower end and an upper end. The handle has an essentially cylindrically shaped central extent between the lower and upper ends. The lower end includes two parallel downwardly extending shoulders with a space there between to receive the proximal end of the blade. A pin spans the shoulders for rotatably supporting the recess of the blade. In this manner the blade may be positioned between an operative position with the blade at a right angle with respect to the handle and an inoperative position when the blade is parallel to the handle. A pivotable latch is included with the blade, spring urged over an associated latch pin on the handle, to hold the blade and handle in the operative position. Depressing the lower end of the pivotal latch will retract the upper end of the pivotal latch away from the latch pin to allow separation of the blade and handle.

Next, a suction subassembly is provided. A tubular passageway in the blade extends from a first end at the distal end of the blade and a second end at a location adjacent to the proximal end of the blade. An elbow has a lower end coupled to the second end and a free upper end. The elbow is secured to one side of the blade laterally spaced. The suction subassembly includes a vertical tube with a recess along the length of the handle. A weep hole is provided in the vertical tube. The weep hole functions to divert suction from the outside atmosphere to the distal end of the blade. Retainers removably secure the tube in the recess. The vertical tube has an upper end adapted to be coupled to a source of negative pressure and a lower end adapted to receive the free end of the elbow when the blade is in the operative orientation and to separate the free end from the tube when the blade is in the inoperative orientation.

Lastly, an optical subassembly is provided. The optical subassembly includes an upper optical strand and a lower optical strand. Each strand has a free end in the distal end of the blade and an input end adjacent to the free end of the elbow. The optical subassembly also includes a housing located adjacent the lower end of the tube. A downwardly facing bulb is provided and a battery is operatively coupled to the bulb. The housing has an associated coil spring adapted to urge the bulb downwardly away from the battery when the blade is in an inoperative orientation and allowing upwardly movement toward the battery allowing contact during an operative orientation. The input ends of the strands are adapted to contact the bulb when the blade is in the operative orientation to thereby illuminate the distal end of the blade. The input ends of the strands are adapted to move out of contact with the bulb and separate therefrom when the blade is in the inoperative position to terminate the illumination of the distal end of the blade.

There has thus been outlined, rather broadly, the more important features of the invention in order that the detailed description thereof that follows may be better understood and in order that the present contribution to the art may be better appreciated. There are, of course, additional features of the invention that will be described hereinafter and which will form the subject matter of the claims attached.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of descriptions and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved laryngoscope system with illuminator and suction capabilities which has all of the advantages of the prior art laryngoscopes of known designs and configurations and none of the disadvantages.

It is another object of the present invention to provide a new and improved laryngoscope system with illuminator and suction capabilities which may be easily and efficiently manufactured and marketed.

It is further object of the present invention to provide a new and improved laryngoscope system with illuminator and suction capabilities which is of durable and reliable constructions.

An even further object of the present invention is to provide a new and improved laryngoscope system with illuminator and suction capabilities which is susceptible of a low cost of manufacture with regard to both materials and labor, and which accordingly is then susceptible of low prices of sale to the consuming public, thereby making such laryngoscope system with illuminator and suction capabilities economically available to the buying public.

Even still another object of the present invention is to provide a laryngoscope system with illuminator and suction capabilities for facilitating endotracheal intubation.

Lastly, it is an object of the present invention to provide a new and improved laryngoscope system having a blade with a distal end, and intermediate extent, and a generally C-shaped recess adjacent to a proximal end. A handle has a lower end, a central extent, and an upper end. The lower end has a space between two parallel shoulders to receive the blade and a pin spanning the space to rotatably support the recess of the blade. A suction subassembly extends between the handle and the blade. An optical subassembly extends between the handle and the blade. The blade subassembly and optical subassembly move between an operative position and inoperative position.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is a magnified view of the present invention taken at circle 3 of FIG. 1 showing the details of the elbow of the suction subassembly.

FIG. 4 is an exploded view of the present invention showing the blade separated from the handle.

FIG. 5 is an elevational view of the blade of the present invention taken alone line 5-5 of FIG. 4.

FIG. 6 is a cross sectional view of the blade of the present invention taken along line 6-6 of FIG. 5.

The same reference numerals refer to the same parts throughout the various Figures.

DESCRIPTION OF THE PREFERRED EMBODIMENT

Figure 1:
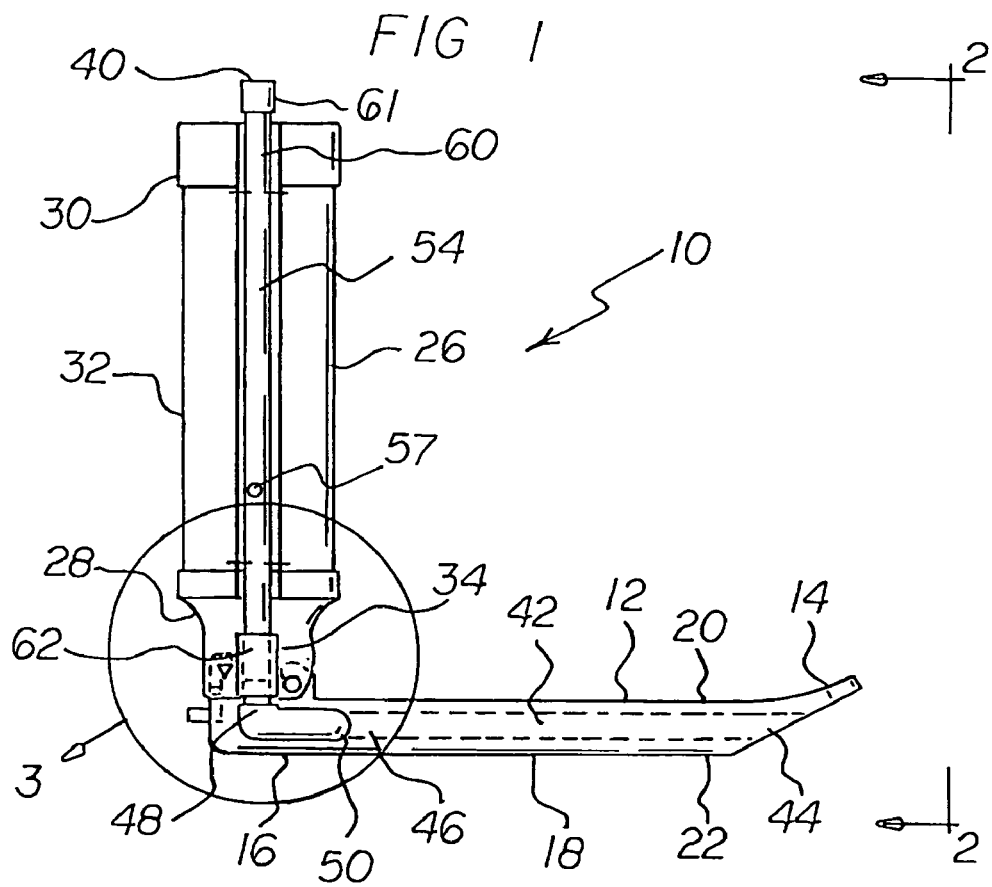
FIG. 1 is a plan view of the laryngoscope system shown in the operative position.
Figure 2:
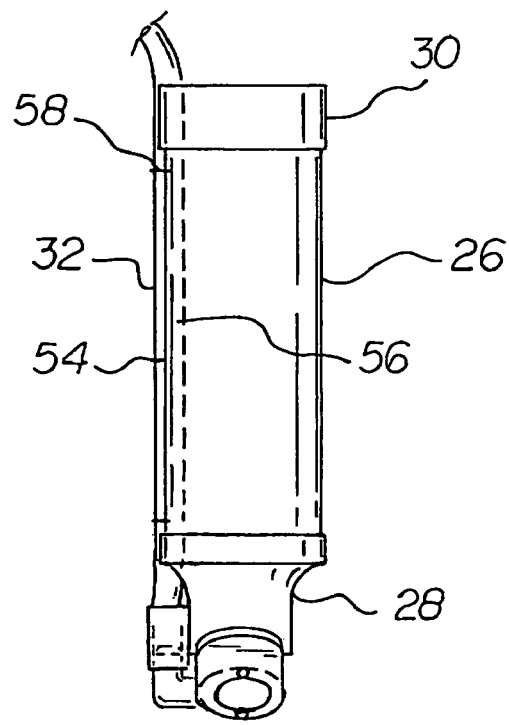
FIG. 2 is a side view of the present system taken along line 2-2 of FIG. 1 illustrating the handle.
Figure 7:
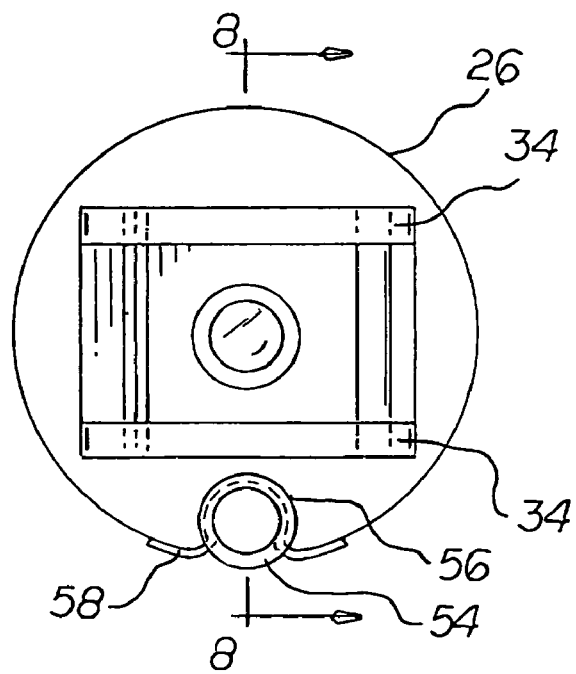
FIG. 7 is an elevational view of the handle of the present invention taken along line 7-7 of FIG. 4.
Figure 8:
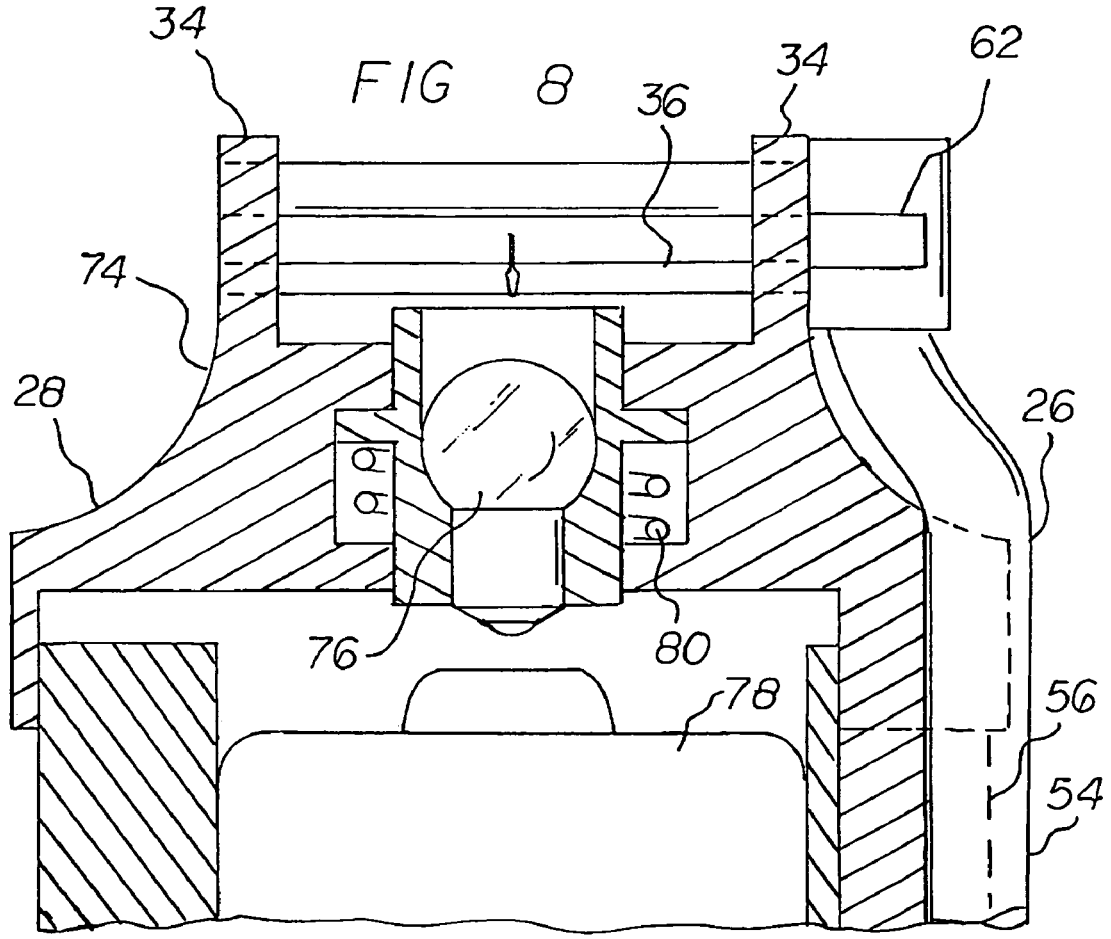
FIG. 8 is a cross sectional view of the handle of the present invention taken along line 8-8 of FIG. 7.

With reference now to the drawings, and in particular to FIG. 1 thereof, the preferred embodiment of the new and improved laryngoscope system with illuminator and suction capabilities embodying the principles and concepts of the present invention and generally designated by the reference numeral 10 will be described.

The present invention, the laryngoscope system with illuminator and suction capabilities 10 is comprised of a plurality of components. Such components in their broadest context include a blade, a handle, a suction subassembly and an optical subassembly. Such components are individually configured and correlated with respect to each other so as to attain the desired objective.

First provided is a blade 12. The blade is fabricated of an essentially rigid, preferably plastic, material. The blade has a distal end 14 positionable in a patient's mouth, a proximal end 16 positionable outside of a patient's mouth. The blade also has an intermediate extent 18 between the proximal and distal ends. The blade has an upper surface 20 positionable on a patient's tongue and a lower surface 22. The blade having a generally C-shaped recess 24 adjacent to the proximal end of the upper surface.

Next provided is a handle 26 fabricated of an essentially rigid, preferably stainless steel, material. The handle has a lower end 28 and an upper end 30. The handle has an essentially cylindrically shaped central extent 32 between the lower and upper ends. The lower end includes two parallel downwardly extending shoulders 34 with a space there between to receive the proximal end of the blade. A pin 36 spans the shoulders for rotatably supporting the recess of the blade. In this manner the blade may be positioned between an operative position with the blade at a right angle with respect to the handle and an inoperative position when the blade is parallel to the handle. A pivotable latch 38 is included with the blade, spring urged over an associated latch pin 37 on the handle, to hold the blade and handle in the operative position. Depressing the lower end of the pivotal latch 38 will retract the upper end of the pivotal latch away from the latch pin to allow separation of the blade and handle.

Next, a suction subassembly 40 is provided. A tubular passageway 42 in the blade extends from a first end 44 at the distal end of the blade and a second end 46 at a location adjacent to the proximal end of the blade. An elbow 48 has a lower end 50 coupled to the second end 52 and a free upper end. The elbow is secured to one side of the blade laterally spaced. The suction subassembly includes a vertical tube 54 with a recess 56 along the length of the handle. A weep hole 57 is provided in the vertical tube. The weep hole functions to divert suction from the outside atmosphere to the distal end of the blade. Retainers 58 removably secure the tube in the recess. The vertical tube has an upper end 60 with an adaptor 61 being able to be coupled to a source of negative pressure using a limited amount of tubing making transport of the system more permissible. A lower end 62 adapted to receive the free end of the elbow when the blade is in the operative orientation and to separate the free end from the tube when the blade is in the inoperative orientation.

Lastly, an optical subassembly 64 is provided. The optical subassembly includes an upper optical strand 66 and a lower optical strand 68. Each strand has a free end 70 in the distal end of the blade and an input end 72 adjacent to the free end of the elbow. The optical subassembly also includes a housing 74 located adjacent the lower end of the tube. A downwardly facing bulb 76 is provided and a battery 78 is operatively coupled to the bulb. The housing has an associated coil spring 80 adapted to urge the bulb downwardly away from the battery when the blade is in an inoperative orientation and allowing upwardly movement toward the battery allowing contact during an operative orientation. The input ends of the strands are adapted to contact the bulb when the blade is in the operative orientation to thereby illuminate the distal end of the blade. The input ends of the strands are adapted to move out of contact with the bulb and separate therefrom when the blade is in the inoperative position to terminate the illumination of the distal end of the blade.

As to the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed is:

1. A laryngoscope system comprising:
   a blade having a distal end and a proximal end with an intermediate extent there between, the blade having a generally C-shaped recess adjacent to the proximal end;
   a handle having a lower end and an upper end and a central extent there between, the lower end including two parallel shoulders with a space there between to receive the blade and a pin spanning the space to rotatably support the recess of the blade;
   an optical subassembly extending between the blade and the handle;
   the blade and handle movable between an operative position wherein the blade is at a right angle with respect to the handle and an inoperative position wherein the blade is parallel to the handle;
   a suction subassembly extending between the blade and the handle including a tubular passageway in the blade extending from a first end at the distal end of the blade to a second end at a location adjacent to the proximal end of the blade with an elbow having a lower end coupled to the second end and a free upper end, the elbow being secured laterally to one side of the blade, the suction subassembly also including a vertical tube with a recess along the length of the handle with retainers to removably secure the tube in the recess, the vertical tube having an upper end adapted to be coupled to a source of negative pressure and a lower end, the lower end adapted to receive the free end of the elbow when the blade is in the operative position and to separate the free end from the tube when the blade is in the inoperative position.

2. A laryngoscope system as set forth in claim 1 wherein the optical subassembly includes an upper optical strand and a lower optical strand, each strand having a free end in the distal end of the blade and an input end adjacent to the free end of the elbow, the optical subassembly also including a housing located adjacent the lower end of the tube with a downwardly facing bulb and a battery operatively coupled to the bulb, the housing having an associated coil spring adapted to urge the bulb downwardly away from the battery when the blade is in an inoperative position and allowing upwardly movement toward the battery allowing contact during an operative position, the input ends of the strands adapted to contact the bulb when the blade is in the operative position to thereby illuminate the distal end of the blade, the input ends of the strands adapted to move out of contact with the bulb and separate therefrom when the blade is in the inoperative position to terminate the illumination of the distal end of the blade.

3. The laryngoscope as set forth in claim 2 wherein the vertical tube is an adaptor adjacent to the upper end of the handle allowing minimal use of tube.

4. A laryngoscope system with illuminator and suction capabilities to facilitate endotracheal intubation comprising, in combination:
   a blade fabricated of plastic having a distal end positionable in a patient's mouth, a proximal end positionable outside of a patient's mouth and an intermediate extent there between, the blade having an upper surface positionable on a patient's tongue and a lower surface, the blade having a generally C-shaped recess adjacent to the proximal end of the upper surface;
   a handle fabricated of steel having a lower end and an upper end with an essentially cylindrically shaped central extent there between, the lower end including two parallel downwardly extending shoulders with a space there between to receive the proximal end of the blade, a pin spanning the shoulders for rotatably supporting the recess of the blade whereby the blade may be positioned between an operative position with the blade at a right angle with respect to the handle and an inoperative position when the blade is parallel to the handle, the blade including a pivotable latch with an associated latch pin on the handle to hold the blade and handle in the operative position;
   a suction subassembly including a tubular passageway in the blade extending from a first end at the distal end of the blade to a second end at a location adjacent to the proximal end of the blade with an elbow having a lower end coupled to the second end and a free upper end, the elbow being secured laterally to one side of the blade, the suction subassembly also including a vertical tube with a recess along the length of the handle with retainers to removably secure the tube in the recess, a weep hole in the tube, the vertical tube having an upper end with an adaptor being able to be coupled to a source of negative pressure adjacent to the upper end of the handle and a lower end, the lower end adapted to receive the free end of the elbow when the blade is in the operative position and to separate the free end from the tube when the blade is in the inoperative position; and an optical subassembly including an upper optical strand and a lower optical strand, each strand having a free end in the distal end of the blade and an input end adjacent to the free end of the elbow, the optical subassembly also including a housing located adjacent the lower end of the tube with a downwardly facing bulb and a battery operatively coupled to the bulb, the housing having an associated coil spring adapted to urge the bulb downwardly away from the battery when the blade is in an inoperative position and allowing upwardly movement toward the battery allowing contact during an operative position, the input ends of the strands adapted to contact the bulb when the blade is in the operative position to thereby illuminate the distal end of the blade, the input ends of the strands adapted to move out of contact with the bulb and separate therefrom when the blade is in the inoperative position to terminate the illumination of the distal end of the blade.

* * * * *